(12) United States Patent
Vau et al.

(10) Patent No.: US 6,540,663 B1
(45) Date of Patent: Apr. 1, 2003

(54) STRESS CONTROL SYSTEM

(75) Inventors: Jean-Marie Vau, Paris (FR); Laurent Ricard, Boulogne-Billancourt (FR)

(73) Assignee: Eastman Kodak Company, Rochester, NY (US)

( * ) Notice: Subject to any disclaimer, the term of this patent is extended or adjusted under 35 U.S.C. 154(b) by 168 days.

(21) Appl. No.: 09/586,862

(22) Filed: Jun. 5, 2000

(30) Foreign Application Priority Data

Oct. 13, 1999 (FR) .............................................. 99 12982

(51) Int. Cl.[7] .............................................. A61M 21/00
(52) U.S. Cl. ........................................ 600/27; 600/301
(58) Field of Search .......................... 600/300, 26, 27, 600/28, 587, 589, 390, 391; 455/304–466; 379/90.01–108.02

(56) References Cited

U.S. PATENT DOCUMENTS

| 5,228,449 A | | 7/1993 | Christ et al. ................ 128/691 |
|---|---|---|---|
| 5,544,661 A | * | 8/1996 | Davis et al. ................. 600/513 |
| 6,102,856 A | * | 8/2000 | Groff et al. .................. 600/301 |
| 6,184,804 B1 | * | 2/2001 | Harrison ....................... 341/22 |
| 6,336,900 B1 | * | 1/2002 | Alleckson et al. ........... 600/485 |
| 6,350,237 B1 | * | 2/2002 | Pelletier et al. ............. 600/300 |

FOREIGN PATENT DOCUMENTS

EP 0 938 866 A1 9/1999 ............ A61B/5/16

* cited by examiner

*Primary Examiner*—Kevin Shaver
*Assistant Examiner*—Pamela Wingood
(74) *Attorney, Agent, or Firm*—David M. Woods

(57) ABSTRACT

The system comprises a server capable of sending images to a cellphone fitted with a display screen and sensors for generating a signal dependent on user's physiological parameters. The series of images supplied by the server is according to the user, by the prior acquisition of a user profile and at least one item of physiological data for this user transmitted by the sensor, so as to change unconsciously the user's psychophysiological state.

4 Claims, 6 Drawing Sheets

STRESS CONTROL SYSTEM

FIELD OF THE INVENTION

The present invention relates to a stress control system comprising the integration of physical or psychophysiological parameters dependent on the state of the individual in a control system, and more particularly to the utilization of these parameters, by a sequential presentation of images chosen according to the parameter values and the individual, for controlling this individual's stress level.

BACKGROUND OF THE INVENTION

It is well known that an individual's physical and psychophysiological state changes certain of this individual's physiological parameters such as, for example, the surface temperature of the individual's skin, the conductivity of the skin, etc. Currently, there are on the market stress control systems based on the utilization of biofeedback techniques, that is, based on the measurement of psychophysiological parameters, together with a presentation of images possibly with sound. This system, distributed by the Ultramind™ company, encourages the user by concentration, to change their psychophysiological state to control a certain type of display. In this system, the surface temperature and/or the surface conductivity of the individual's skin is utilized to control the presentation's content and display. Such a system currently operates in a PC environment requiring a bulky interface to capture the physiological parameters.

SUMMARY OF THE INVENTION

The present invention operates in a different way than the system distributed by Ultramind™. In the embodiment according to the invention, the presentation of biofeedback data, that is, based on the individual's psychophysiological parameters, acts automatically on the individual to transform their psychophysiological state.

The present invention aims to make the control system "nomadic", that is utilizable anywhere, and at any time.

The present invention also enables a person's psychophysiological state control system to be personalized, that is to calibrate the response supplied by the system according to each person.

The present invention again enables personalization not only of the presentation supplied by the system, but also the interface used to capture and process the physiological parameters, for example by the utilization of a mobile telephone.

The present invention also provides greater efficiency in stress control by a wide choice of usable images, thanks to the utilization of a powerful image base, bulky and difficult to load on a simple PC, and still less on a very light client station (for example a cellphone).

The present invention also enables algorithms to be run that would be difficult to produce on a very light client (for example, a cellular telephone), thanks to the utilization of a server with very high calculating power.

The starting up time in a dedicated and personalized system, that is presenting a specific function and not requiring the "invasive" connection of biophysiological sensors, can be greatly reduced because overlong starting up is a serious brake to the repeated utilization of a biofeedback system (lassitude effect in relation to the system).

The present invention also guarantees the privacy desirable for each individual by the utilization of a cellphone, an object that is hardly ever lent.

The present invention also enables the actual utilization of the system according to the invention to be known through the utilization of a cellphone.

The objects of the invention are obtained by a control system for a user's psychophysiological state, comprising: a) a remote server supplied with; a1) a remote communication system to exchange digital data; a2) an image base; and a3) an inference engine to determine which digital data representing images to transmit; b) at least one sensor in contact with the user, the sensor being linked to an electronic transmission unit so as to supply a signal relating to one item of the individual's physiological data to the inference engine; and c) operating on a mobile client linked to the server, with a displayer for digital data coming from the server, the series of images supplied by the server being according to the user and the physiological data.

The objects of the invention are also obtained by the utilization of a cellphone to control an individual's psychophysiological state, in which the cellphone comprises sensors in contact with the user's skin to generate a signal representing at least one item of the user's physiological data and a display screen for showing a series of images, the said series of images being according to the user and the physiological data.

The objects of the present invention are also obtained by means of a transformation kit for a cellphone capable of being linked to a digital data network comprising at least one sensor intended to make contact with the user's skin and a socket adapted so as to be able to transmit the signal from the sensor inside the cellphone in order to send this signal to the server to order the series of images transmitted by the server according to the user's profile and the physiological data supplied by the sensor with a view to obtaining a control system for the user's psychophysiological state.

BRIEF DESCRIPTION OF THE DRAWINGS

The foregoing and other objects, features, and advantages of the invention will be apparent from the following more particular description of the preferred embodiments of the invention, as illustrated in the accompanying drawings.

DETAILED DESCRIPTION OF THE INVENTION

Figure 1:
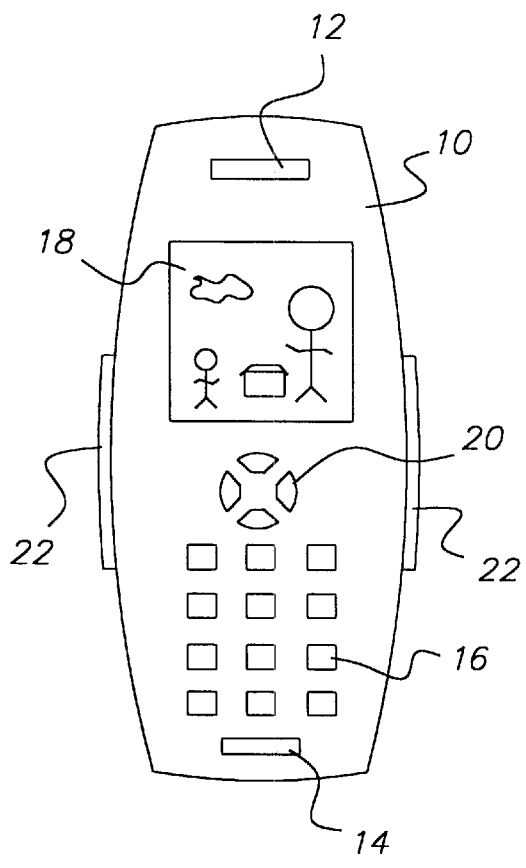
FIG. 1 represents a conventional cellphone, capable of being connected to a data network transmitting biofeedback type information, equipped with a detection module for an individual's physiological data.

The following is a detailed description of the preferred embodiments of the invention, reference being made to the drawings in which the same reference numerals identify the same elements of structure in each of the several figures.

Figure 4:
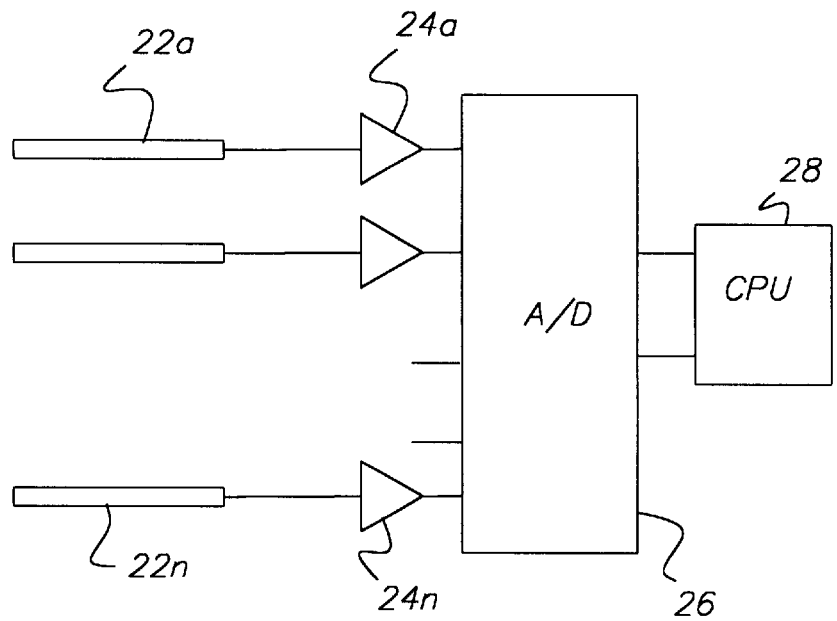
FIG. 4 represents an embodiment of an amplification and conversion circuit that can be used by the invention.

In one embodiment of the invention, a cellphone is utilized as an assembly providing, in contact with the user, sensors for sensing physiological data relating to this user. As can be seen in FIG. 1, the cellphone is capable of being linked to a data network such as, for example, the internet. It comprises a case 10, whose general shape is close to a more or less distorted rectangular parallelepiped, with an easy grip. The case comprises, for example, an earpiece 12 and a microphone 14 as well as keys 16 for exchanging information with a central processing unit 28 (FIG. 4). In cellphones capable of being linked to a data network the case comprises a display screen 18 and navigation buttons 20. According to the invention, the case is fitted with sensors 22 for sensing physiological data relating to the user; these sensors may be arranged on either side of the case to be in contact with a user's hand while holding the cellphone. The number of sensors 22a–22n (FIG. 4) will depend on the application, the type of physiological data to be captured by the sensors, for example temperature, conductivity, etc.

Figure 3:
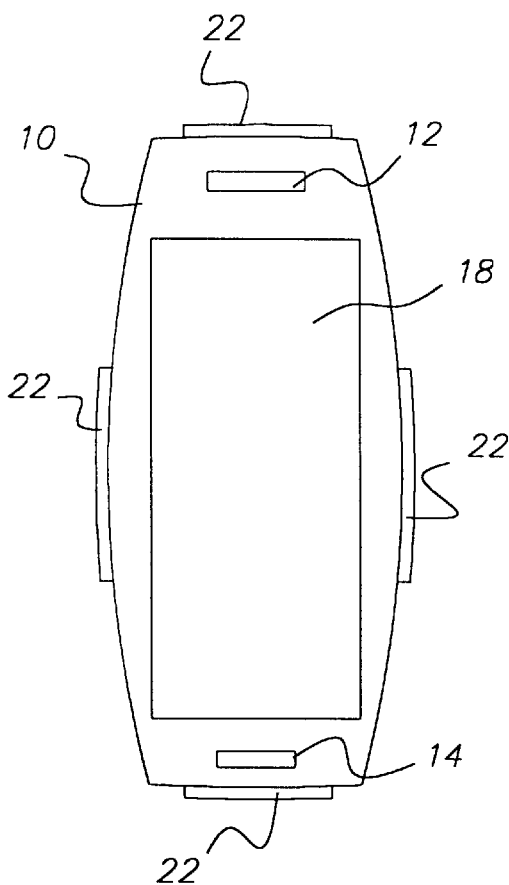
FIG. 3 represents another embodiment of a cellphone that can be used according to the invention.
Figure 2:
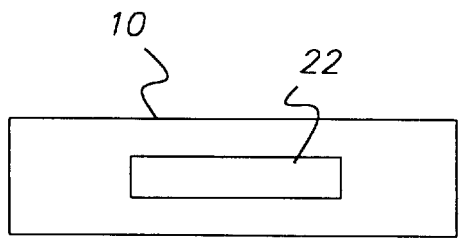
FIG. 2 represents the cellphone of FIG. 1 seen in profile.

In another embodiment, represented in FIG. 3, the display screen 18 has a size taking up most of the cellphone's main face, which enables utilization in a landscape mode. The screen could be, for example, a touch screen having associated zones (not shown) supplying the navigation buttons 20 and the keys 16. The sensors for sensing physiological data 22 are located according to the user's grip and, as shown in FIG. 3, can be in two pairs, each pair being arranged on two practically parallel sides of the case.

As can be seen in FIG. 4, each sensor 22a–22n is linked to an electronic amplification unit 24a–24n and an A/D conversion unit 26, enabling each analog signal to be transformed into a digital signal and each digital signal to be transmitted to the processing unit 28.

Figure 5:
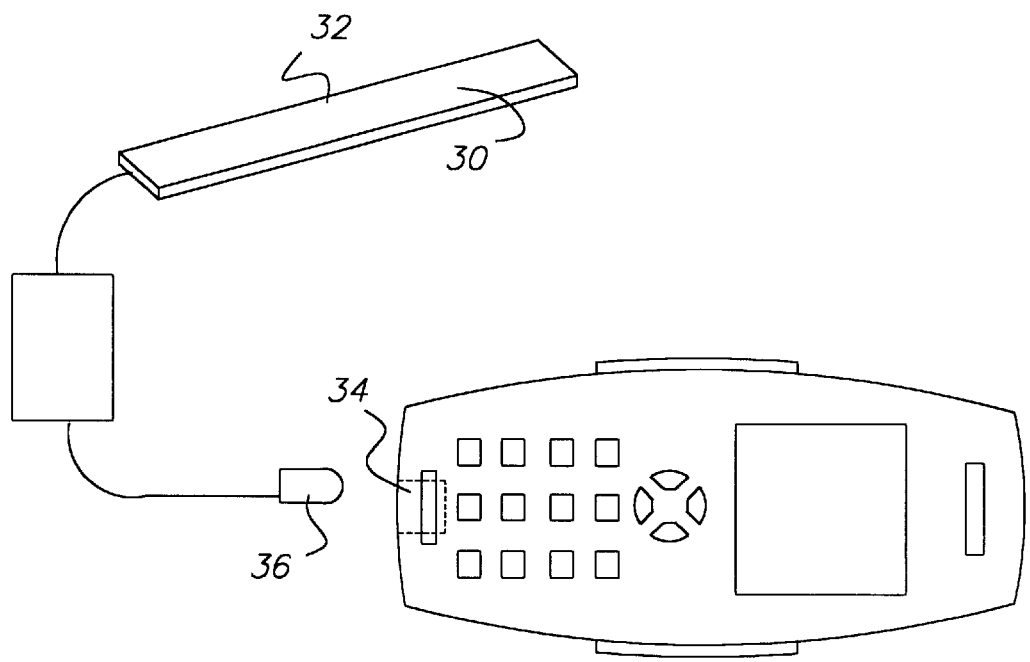
FIG. 5 represents a possible embodiment of the amplification and conversion circuit enabling a cellphone to be equipped with a biofeedback function.

As can be seen in FIG. 5, with a particular embodiment, cellphones capable of being linked to a data network can be equipped with a detection device for sensing physiological data comprising at least one detection electrode 30 having an adhesive surface 32 that can be bonded to the case 10. This electrode 30 is linked by an amplification unit 24 and a conversion unit 26 to an input port 34 of the case 10 by means of an appropriate socket 36, for example, a USB or analog type of socket.

Figure 6:
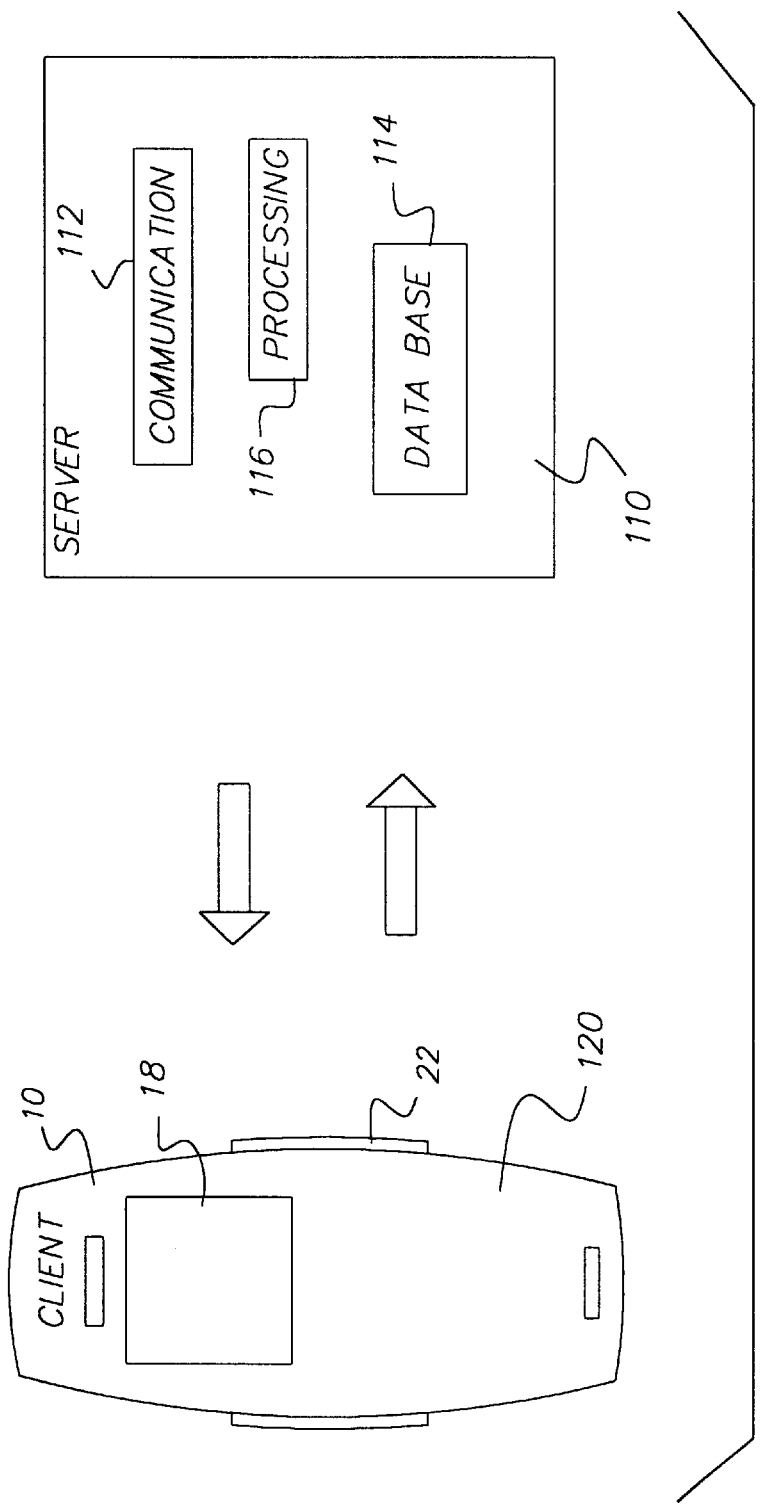
FIG. 6 represents a client-server system based on implementation of the invention.

In one particularly advantageous embodiment, a client-server architecture can be chosen, as shown in diagram form in FIG. 6 in which the cellphone is a client 120 that communicates across a network with a server 110. This architecture enables the mobility of the invention to be increased by deporting to the maximum the digital archiving of images and sound as well as the calculation power necessary to implement the anti-stress algorithm. More specifically, the remote server 110 includes a remote communication system 112 for exchanging digital data with the client 120, a digital database 114 for storing images, and a processing section 116 providing an inference search engine for determining which images to retrieve from the database 116.

In another particularly advantageous embodiment, the cellphone comprises a socket to connect a listening accessory that can be put in the ear and which enables the cellphone's screen to be looked at while listening to the sound transmitted simultaneously with the images by the digital data coming from the server.

Figure 7:
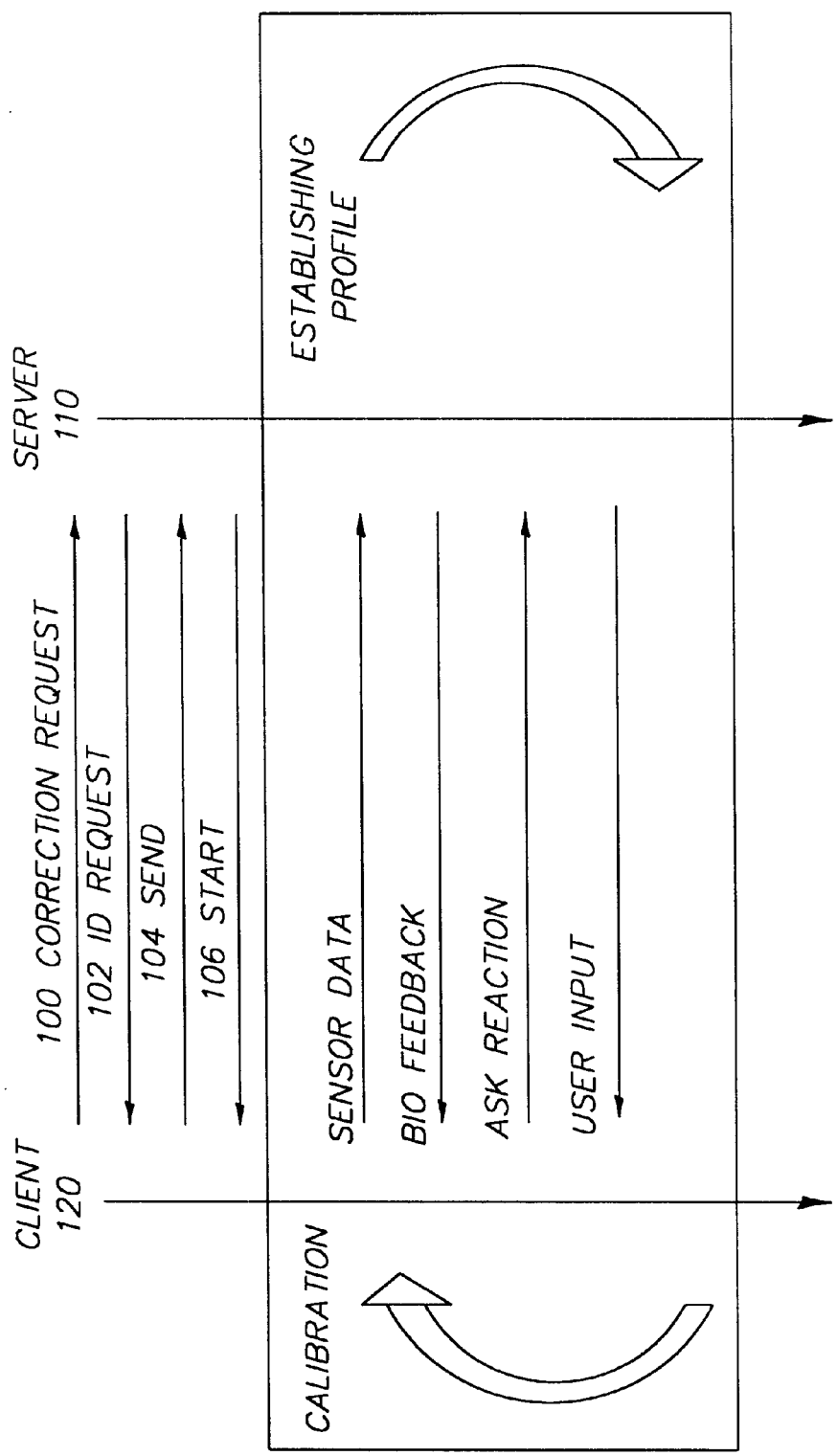
FIG. 7 represents diagrammatically the main access and exchanges of data utilized in a first implementation of the invention.

As can be seen in FIG. 7, which describes the main communication steps between the client 120, incorporated in the case 10, and the server 110, the invention starts with a link request 100 to the remote server 110. After the request 102 for an ID by the server 110 and the sending 104 of this ID, the server 110 starts (106) the application.

According to the invention, the application enables a presentation of images, optionally with sound, to be controlled according to the physiological parameters supplied by the sensors in contact with the user in order to control this individual's stress level at the moment of use. To obtain an effective level of anti-stress treatment, the choice of the series of images is personalized, that is dependent on the user's signature. To determine the user's signature, the system has to be calibrated according to this user.

In a first phase, named the calibration phase and shown in diagram form in FIG. 7, the server offers to a user, whose signature is as yet unknown, reference images for which this user has to supply a conscious response. For instance the response can consist of: "I like/don't like the image, it calms me, it irritates me, etc.". Clearly the server can offer a choice of responses to be checked. The correlation of the responses with the images and the physiological data determines the user's profile, which may either be named user's signature or user's profile.

Figure 8:
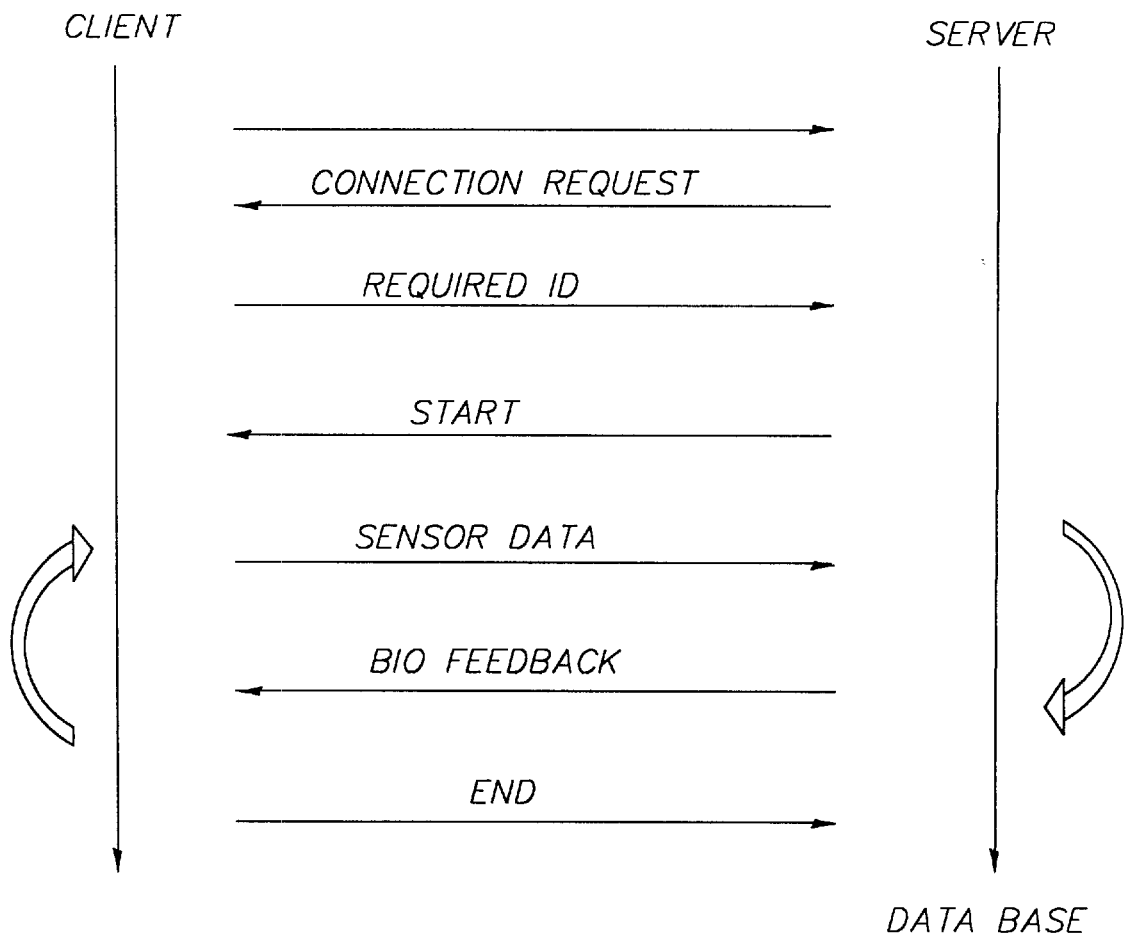
FIG. 8 represents diagrammatically the main access and transfers of data in a further implementation.
Figure 9:
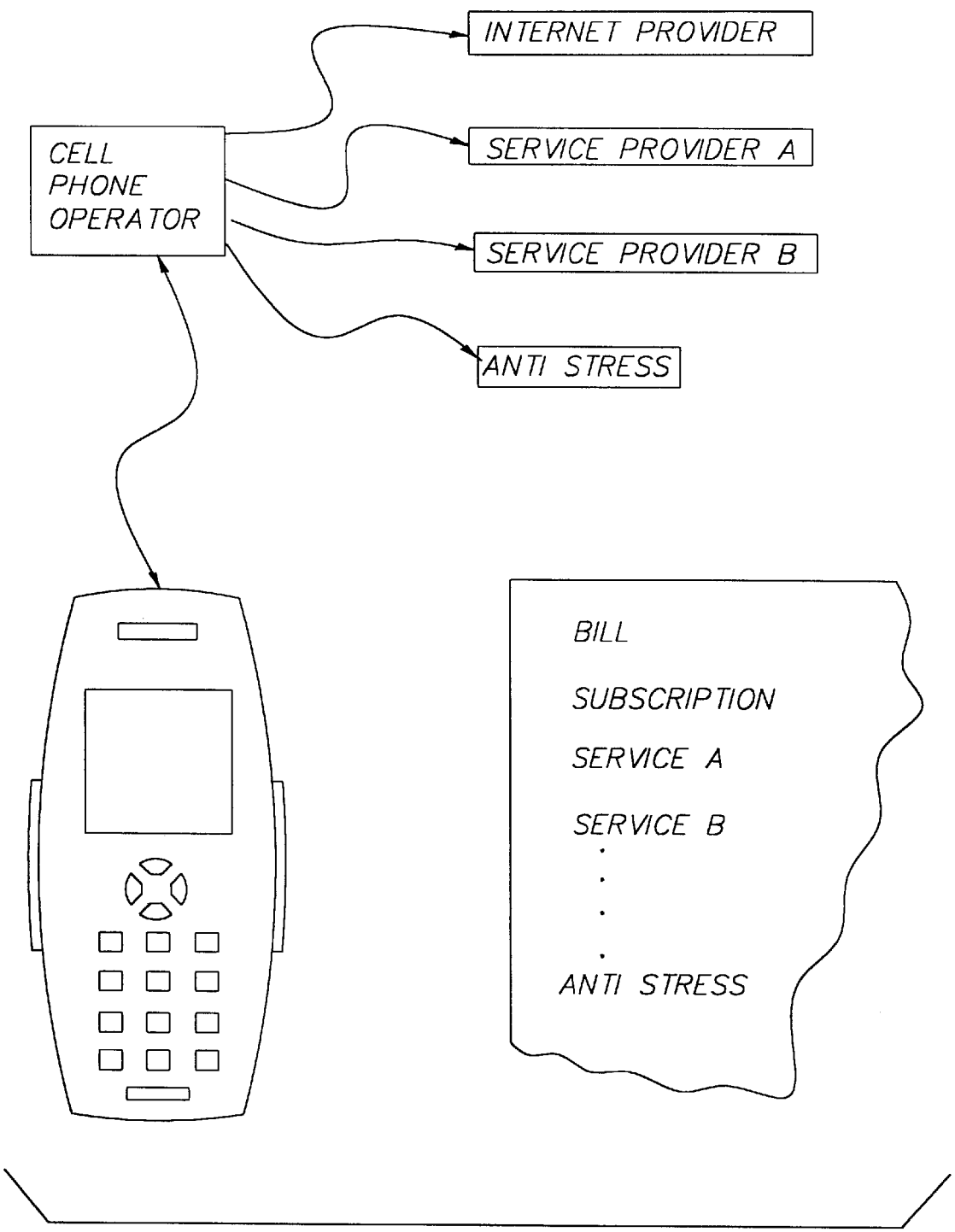
FIG. 9 represents a possible commercial operating model for the invention.

At a later utilization, the user's signature having already been determined, the server offers images according to the responses given during the creation of the user's profile and the physiological parameters transmitted in real time by the client 120 as represented in FIG. 8.

It is well known that cellphones are distributed by telephone operators (Itineris™, SFR™, Bouygues™, AirTouch™ (US), Vodafone™ (UK), etc.) which supply their subscribers with a bill detailing the types of service. For example, the bill will include a line relating to the subscription, a line for each service called (Weather, Stock exchange, etc.).

The telephone operator usually calls on service providers who provide the service content. For instance, AOL™ or Wanadoo™ can be called on to manage e-mail or access the Yellow Pages. The anti-stress service is available in the same way and at each billing a percentage of the bill will be repaid to the service provider.

The invention and its operation provides users with a portable system, enabling them to change their psychophysiological state and in particular to reduce their stress, and whose payment is proportional to their utilization.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A control system for a user's psychophysiological state, comprising:
   a) a remote server supplied with:
      a1) a remote communication system to exchange digital data;
      a2) a digital database to represent and store images; and
      a3) an interference engine to determine which digital data representing images to transmit;
   b) a mobile client incorporated in a case and linked to said server, said mobile client supplied with:
      b1) at least one sensor attached to the case, said sensor being in contact with the user and being linked to an electronic transmission unit so as to supply a signal, relating to at least one item of the user's physiological data, to said inference engine; and b2) a display for digital data communicated from said server, whereby said digital data comprises a series of images supplied by said server being related to said user and said physiological data.

2. A method for utilizing a cellphone capable of being linked to a digital data network to control an individual's psychophysiological state, comprising the steps of contacting the user's skin with sensors in said cellphone to generate a signal representing at least one item of the user's physiological data, and showing a series of images on a display on said cellphone, said series of images being selected according to said user and said physiological data.

3. A transformation kit for a cellphone capable of being linked to a digital data network in a control system for evaluating an individual's psychophysiological state, said kit comprising a combination in kit form including at least one sensor intended to make contact with the user's skin and generate a signal representing said individual's psychophysiological state, and a socket adapted so as to be able to transmit the signal from said at least one sensor to said cellphone.

4. A kit according to claim 3, comprising in addition an adaptation circuit to transform an analog signal coming from said sensor into a digital signal.

* * * * *

UNITED STATES PATENT AND TRADEMARK OFFICE
CERTIFICATE OF CORRECTION

PATENT NO.      : 6,540,663 B1
DATED           : April 1, 2003
INVENTOR(S)     : Jean-Marie Vau et al.

It is certified that error appears in the above-identified patent and that said Letters Patent is hereby corrected as shown below:

<u>Column 6,</u>
Line 7, after "representing said individual's psychophysiological state" please add -- said signal initiating a series of images on a display on said cellphone, said series of images being selected according to said individual's psychophysiological state --

Signed and Sealed this

Twenty-ninth Day of July, 2003

JAMES E. ROGAN
*Director of the United States Patent and Trademark Office*